United States Patent
Atkinson

(10) Patent No.: US 10,996,494 B2
(45) Date of Patent: May 4, 2021

(54) DEVICE AND METHOD TO FIX A MESSAGE ON A DISPLAY

(71) Applicant: Paul Atkinson, Poway, CA (US)

(72) Inventor: Paul Atkinson, Poway, CA (US)

(73) Assignee: Chromera, Inc., Poway, CA (US)

( * ) Notice: Subject to any disclaimer, the term of this patent is extended or adjusted under 35 U.S.C. 154(b) by 326 days.

(21) Appl. No.: 16/186,509

(22) Filed: Nov. 10, 2018

(65) Prior Publication Data

US 2020/0152106 A1 May 14, 2020
US 2021/0104189 A9 Apr. 8, 2021

Related U.S. Application Data

(63) Continuation of application No. 14/797,141, filed on Jul. 12, 2015, now Pat. No. 10,156,763.

(60) Provisional application No. 62/182,127, filed on Jun. 19, 2015.

(51) Int. Cl.
| | |
|---|---|
| *G02F 1/01* | (2006.01) |
| *G02F 1/155* | (2006.01) |
| *G02F 1/163* | (2006.01) |
| *G09G 3/19* | (2006.01) |
| *G06Q 10/08* | (2012.01) |
| *G16H 40/20* | (2018.01) |

(52) U.S. Cl.
CPC .......... *G02F 1/0121* (2013.01); *G02F 1/155* (2013.01); *G02F 1/163* (2013.01); *G09G 3/19* (2013.01); *G02F 2201/124* (2013.01); *G06Q 10/0832* (2013.01); *G09G 2310/0254* (2013.01); *G09G 2380/04* (2013.01); *G16H 40/20* (2018.01)

(58) Field of Classification Search
CPC .......... G02F 1/163; G02F 1/153; G02F 1/155; G02F 1/0121
See application file for complete search history.

(56) References Cited

U.S. PATENT DOCUMENTS

| | | | | |
|---|---|---|---|---|
| 7,599,109 | B2 * | 10/2009 | Champion | G02F 1/15 359/275 |
| 7,990,515 | B2 * | 8/2011 | Mi | B44F 1/10 349/177 |
| 8,018,347 | B2 * | 9/2011 | Tehrani | G04F 13/04 340/588 |
| 10,156,763 | B2 * | 12/2018 | Atkinson | G02F 1/155 |
| 2007/0121190 | A1 * | 5/2007 | Meinders | G02F 1/163 359/265 |
| 2012/0080321 | A1 * | 4/2012 | Thomas | G04F 13/04 205/640 |

\* cited by examiner

*Primary Examiner* — Zachary W Wilkes

(57) ABSTRACT

Briefly, an intelligent label is disclosed that has two viewable surfaces. Each surface is constructed such that a permanent and irreversible message may be set into each surface independently. That is, a first message may be set into the first viewing surface of the electro-optic material, and another message may be set into the second viewing surface, for example, at a later time. Various constructions are described including a construction using two pairs of stimulating electrodes, and a second construction using a single pair of stimulating electrodes.

12 Claims, 9 Drawing Sheets

First, bottom, message   Second, bottom, message   Compound message

DEVICE AND METHOD TO FIX A MESSAGE ON A DISPLAY

RELATED APPLICATIONS

This application is a continuation of U.S. patent application Ser. No. 14/797,141, now U.S. Pat. No. 10,156,763, filed Jul. 12, 2015 and entitled "Device and Method to Fix a Message on a Display," which claims priority to U.S. provisional application No. 62/182,127, filed Jun. 19, 2015, and entitled "Advanced Intelligent Label Device and Method; Device and Method to Modify a Message on an Intelligent Label," both of which are incorporated herein as if set forth in its entirety.

FIELD OF THE INVENTION

The present inventions relates to electro-optic devices for setting a first permanent and irreversible message on one surface of an intelligent label, and then at a second time, setting a second permanent and irreversible message on another surface of the intelligent label.

BACKGROUND

Modern commerce is increasingly dependent on transporting goods using carriers as society embraces more and more online shopping. For example, modern consumers are increasingly using online shopping and common carriers for delivering wine, prescription medication, food, and sensitive electronic devices. To assist in tracking and monitoring the movement of sensitive and expensive goods, labels have been developed in the past that incorporate RFID communication and intelligence. In this way, at the point of shipment and throughout the major carriers, the good has the ability to be tracked. However, adoption of such RFID labels has been slow, as the equipment for initializing, loading, updating, and interrogating the label's RFID electronics is expensive, and typically only available at larger transfer points in the shipping transaction. Further, it is unlikely, and even rare, for the end consumer to be able to interact with the label. Since the consumer is a critical part of the delivery chain, and the consumer is excluded from participation in the information available on the label, the use of intelligent labels has been quite low and very ineffective in improving the customer experience.

In U.S. patent application Ser. No. 14/479,055, entitled "An Intelligent Label Device and Method," which is incorporated herein, a new intelligent label is described. An intelligent label is associated with a good, and includes one or more permanent and irreversible electro-optic devices that are used to report the condition of that good at selected points in the movement or usage of that good. These electro-optic devices provide immediate visual information regarding the good without need to interrogate or communicate with the electronics or processor on the intelligent label. In this way, anyone in the shipping or use chain for the good, including the end user consumer, can quickly understand whether the product is meeting shipping and quality standards. If a product fails to meet shipping or quality standards, the particular point where the product failed can be quickly and easily identified, and information can be used to assure the consumer remains safe, while providing essential information for improving the shipping process. It will be understood that the intelligent label may take many forms, such as a tag attached to the good, integrated into the packaging for the good, integrated into the good itself, or may even be an information area on a prepaid card for example. The intelligent label may also include, for example, print information regarding the good, usage or shipping rules, or address and coded information.

In a particular construction, the intelligent label includes a computer processor for managing the overall electronic and communication processes on the intelligent label. For example, the processor controls any RFID communication, as well as storage of information data. The processor also has a clock, which may be used to accurately identify when the good changed hands in the shipping chain, or when the good failed to meet a quality standard. In this regard, the intelligent label may also have one or more sensors that can detect a chemical or gaseous composition, optical, electrical or an environmental condition such as temperature, humidity, altitude, or vibration. If the processor determines that the sensor has a condition that exceeds the safe handling characteristics, then the processor may store information regarding the out-of-specification handling, and may take additional actions as necessary. For example, if the out-of-specification handling is minimal, the processor may cause an electro-optic device such as an electrochromic indicator or display to show a "caution" as to using the product. In another example, the processor may determine that the sensor has greatly exceeded the outer specification criteria, and cause an electro-optic indicator to show that the product is spoiled or otherwise unusable. Note that the term 'display' as used herein is to be understood to encompass indicators and other electro-optic devices capable of displaying visually perceptible states, data, information, patterns, images, shapes, symbols etc. which are collectively referred to herein as "messages".

The intelligent label may also be constructed with an actuator that can robustly determine the time when the label was attached to the good. For example, the removal of the adhesive backing from a label may make or break an electronic circuit that causes the processor to identify the time when the label adhesive was removed or when the label was attached for shipping. In another example, the actuator can determine when a shipping package was sealed for shipping. Since this action necessarily happens within moments of the label being attached to the good, there is an accurate and traceable time as to when the good was placed by the shipper into the shipping chain. Thereafter, RFID communications may be used to retrieve and load additional information with the label, in order to track the good through the shipping chain.

Advantageously, the intelligent label provides a robust, trustworthy, easily usable system for tracking goods from a point of origin to delivery to the consumer. Importantly, the intelligent label provides important visual alerts, updates and information throughout the shipping process without the need for expensive communication, RFID, or interrogation equipment. Further, the intelligent label facilitates simple and reliable communication of shipping information from a consumer back to a manufacturer or seller, for example, for confirming warranty or replacement information. In this way, a shipping and delivery system having a high degree of trust, and resistance to fraud, is enabled.

In U.S. patent application Ser. Nos. 14/551,600 and 14/569,760, both entitled "Intelligent Label Processing System," which are incorporated herein, a network system is described for advantageously using the new intelligent label. The new network processing system collects and coordinates key indicators regarding a good's condition or quality as that good moves from a supplier to an end user. It will be understood that the supplier may be the manufacturer of the product, or it may be a retailer or distributor or the product. It will also be understood that the terms "good" and "product" may be used interchangeably herein. By collecting more complete information regarding the good and its delivery path, the processing system provides robust, authentic, and trustworthy data that (1) reports the time and/or the time period when third parties, e.g. distributors, resellers and shippers, had custody of the good, (2) identifies what timing or environmental condition caused changes in the condition of the good, and (3) verifies which party had possession of the good when the changes occurred. In use, an intelligent label is attached to a good, and the intelligent label has a timer or real-time clock and/or one or more sensors for monitoring environmental conditions. Upon exceeding timing or environmental rules, a visual indicator is activated on the label. The intelligent label further has electronically retrievable data, scannable or machine readable data, and human readable data, which enables the network process to collect key data regarding the good along the entire distribution chain.

In operation, an intelligent label is associated with a good, and includes one or more preferably permanent and irreversible electro-optic displays that are used to report the condition of that good at selected points in the movement or usage of that good. These electro-optic displays provide immediate visual information regarding the status of the good without need to interrogate or communicate with the electronics or processor on the intelligent label. In this way, anyone in the shipping or use chain for the good, including the end user consumer, can quickly understand the condition of the goods (e.g. ascertain whether the good is meeting shipping and quality standards, and to what extent). If the condition of the good warrants an action (e.g. the condition has degraded and fails to meet shipping or quality standards) the particular time and custodian of the good, when the condition of the good changed to the extent that action is warranted can be quickly and easily identified, and information can be used to enable the appropriate action to be taken (e.g. the goods are not used or consumed, the goods are properly dispose or replaced, a return authorization or credit is issued etc.). In many cases the appropriate action requires that this information is made available to one or more parties and its veracity appropriately verifiable to enable its use to drive business rules and respond to the change(s) in conditions as appropriate to the circumstances (e.g. the good, the change in conditions, the buyer, seller etc.).

In some cases, however, it is desirable that a display be viewable from both a front side and a back side. In this way, information can be displayed to different viewers, and this information can be the same or different. Further, it may be desirable to update or modify the information on the permanent display, which is particularly challenging as the message is intentionally constructed to be permanent and unchangeable.

A particularly difficult problem occurs when a permanent and irreversible message has been set on the intelligent label, and then something occurs, either external or internal to the good or label, that makes the message no longer correct. For example, a prescription drug with an intelligent label may have been sent to consumer with the intelligent label having a permanent and irreversible message set that indicates a particular expiration date. However, after the good has been shipped it is discovered that the experimental drug deteriorates much faster than expected, and the expiration date is wrong. Because the label's message is permanent and irreversible, the provider has no alternative but to recall the drug and re-package or re-label it, which is expensive and may cause harm to the patient due to delayed receipt of good medicine, or if the patient should wrongly take the expired medication. Accordingly, there exists a need to obliterate or change or supplement a message that is incorrect or misleading.

SUMMARY OF THE INVENTION

An intelligent label is provided that has an electro-optic display that consists in part of an irreversible electro-optic layer that has two viewable message surfaces. Each message surface of the electro-optic layer is constructed such that a permanent and irreversible message may be set into each message surface independently. That is, a first message may be set into the first message surface of the electro-optic layer, and another message may be set into the second message surface, for example, at a later time. Various constructions are described including a construction using two pairs of activating electrodes, and a second construction using a single pair of activating electrodes.

An intelligent label is described that has a message that can be permanently and irreversibly set on one message surface of the electro-optic layer. Advantageously, the intelligent label provides a second message surface on the opposite side of the electro-optic layer that can be used in a variety of ways depending on the particular construction selected. In a first use, an opaque electro-optic layer separates the first and second message surfaces. In this way, a separate and distinct message can be placed on either surface, and the intelligent label is usefully viewed from both sides. In some cases it may be useful to have the same message projected on both message surfaces, and in other cases the message surfaces may have different messages set. In a second use, the second message on the second message surface of the electro-optic layer acts to adjust, supplement, or change the message that is set on the first message surface. In this case, the intelligent label is viewed from one direction, and a first message is set into the first message surface. Later, additional characters, symbols, lines, or colors can be set into the second message surface such that a viewer or reader sees the combined effect of the two messages.

In another example, an intelligent label is used that has a message that can be permanently and irreversibly set on one message surface. If at some later time that message becomes incorrect, false, or misleading, then the intelligent label is constructed to permit that message to be obliterated in a way that renders the information in the message unusable, nonsensical, null or unreadable. In one example construction, the intelligent label has an electro-optic display comprising in part an electro-optic material layer that is arranged for dual surface activation. That is, a first activation sets a first message on a first message surface of the electro-optic layer, for example an expiration date, and at a later time, a second activation sets a second message on a second message surface of the electro-optic layer, for example an opaque shape that can partially or fully visually impair or obscure the first message, the expiration date. This obscuring message can take any of several forms, such as a crosshatch pattern or solid shape. In another example construction, the intelligent label has an electro-optic layer that is arranged for single surface activation. In this construction, a first activation sets selected segments to form a message, and at a later time in a second activation, other segments are set to make the message nonsensical or unreadable.

In operation, an intelligent label is associated with a good, and includes one or more, preferably permanent and irreversible electro-optic displays that are used to report the condition of that good at selected points in the movement or usage of that good. These electro-optic displays provide immediate visual information regarding the status of the good without need to interrogate or communicate with the electronics or processor on the intelligent label. In this way, anyone in the shipping or use chain for the good, including the end user consumer, can quickly understand the condition of the goods (e.g. ascertain whether the good is meeting shipping and quality standards, and to what extent). If the condition of the good warrants an action (e.g. the condition has degraded and fails to meet shipping or quality standards) the particular time and custodian of the good, when the condition of the good changed to the extent that action is warranted can be quickly and easily identified, and information can be used to enable the appropriate action to be taken (e.g. the goods are not used or consumed, the goods are properly dispose or replaced, a return authorization or credit is issued etc.). In many cases the appropriate action requires that this information is made available to one or more parties and its veracity appropriately verifiable to enable its use to drive business rules and respond to the change(s) in conditions as appropriate to the circumstances (e.g. the good, the change in conditions, the buyer, seller etc.).

If at a later time the message set by the intelligent label is found to be incorrect or incomplete, then that message as viewed or read can be changed. The intelligent label has sufficient intelligence and power to perform the second change activation, which may be responsive to a communication received wirelessly by the intelligent label, or may be due to some internal stimulus such as elapsed time or a sensed environmental condition.

BRIEF DESCRIPTION OF DRAWINGS

These and other objects and advantages of the invention will become apparent upon reading the following detailed description and upon referring to the drawings in which.

Figure 1:
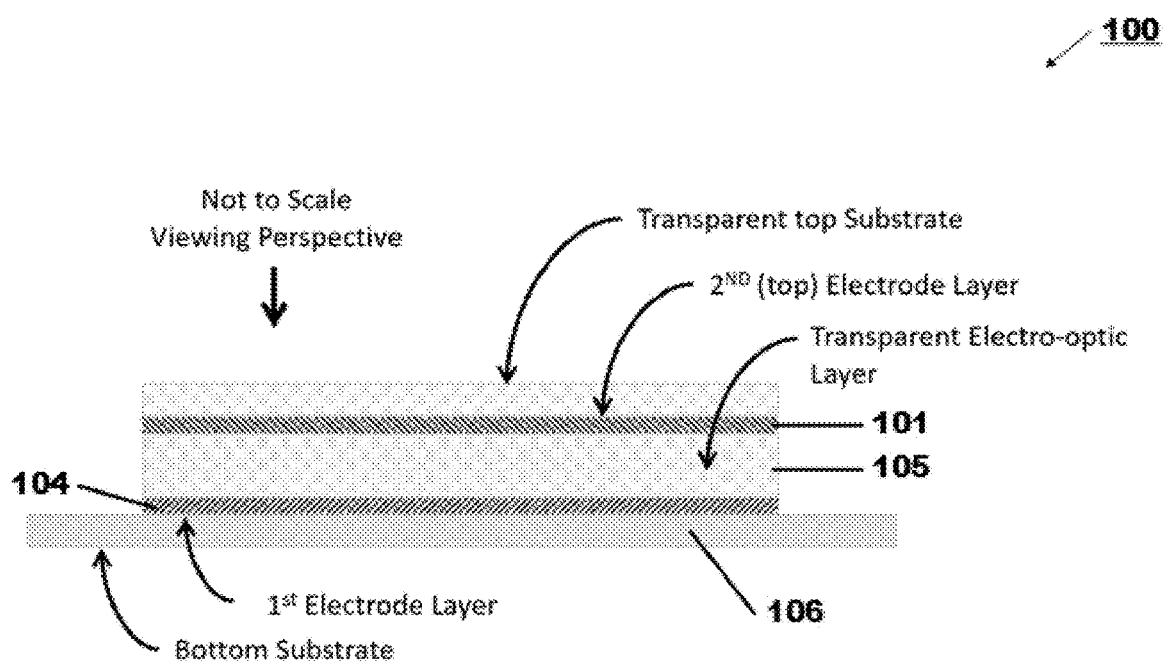
FIG. 1 is a block diagram of a side view of a display device in accordance with the present invention.

While the invention will be described in conjunction with example embodiments, it will be understood that it is not intended to limit the invention to such embodiments. On the contrary, it is intended to cover all alternatives, modifications and equivalents as may be included within the spirit and scope of the invention. It will be understood that the drawings are not to scale, and are simplified to focus the descriptions and discussions on the inventive processes and structures disclosed herein.

DETAILED DESCRIPTION

The following description of exemplary embodiments of the invention is not intended to limit the scope of the invention to these exemplary embodiments, but rather to enable any person skilled in the art to make and use the invention.

An intelligent label is associated with a good, and includes one or more permanent and irreversible electro-optic displays with an electrochromic electro-optic layer such as that described in U.S. Pat. No. 9,030,724, titled "Flexible and Printable Electrooptic Devices," that are used to report the condition of that good at selected times and points in the movement or usage of that good. U.S. Pat. No. 9,030,724 is incorporated by reference as if fully set forth herein. These electro-optic displays provide immediate visual information, messages, regarding the status or condition of the good without need to interrogate or communicate with the electronics or processor on the intelligent label. In this way, anyone in the shipping or use chain for the good, including the end user consumer, can quickly ascertain the condition or state of the good and related time and environmental data that enables the appropriate parties to act or effect on one or more transactions accordingly.

For the messages perceived from the electro-optic display to be of value in improving the distribution of goods or in responding to a customer complaint, the messages must be available and verifiable by the parties who are then enabled to take action. For example, a pharmaceutical package shipped from a manufacturer directly to a consumer may be out of specification when it is delivered if the package has been exposed to a temperature higher than a certain threshold during transit. If this were the case, the simplest action for the consumer and for the supplier might be to immediately distribute a new pharmaceutical package to the consumer and for the consumer to dispose of the original package (and pharmaceuticals). However, there are risks in this situation. A consumer may indicate to the pharmaceutical supplier that this condition existed when it did not, and further that they disposed of the original package and pharmaceuticals when they did not. As a result the consumer would receive two products for the price of one, and importantly the consumer may be tempted to consume dangerous levels of the pharmaceutical or distribute it illicitly without anyone being the wiser.

To avoid these risks the pharmaceutical supplier needs to be able to verify that the original pharmaceuticals are indeed out of specification and also that they are disposed of properly. In addition, the pharmaceutical supplier would like to be able to verifiably determine when the out-of-temperature event occurred and which party had custody of the goods when it happened and for how long, as there may have been multiple potential parties involved in the distribution chain and the financial and remedial responsibility for this out-of-specification condition may belong to only one of the parties (including the consumer). This, and other electronically and optically accessible data from the label, also facilitates efficient and effective procedures for returning the out of specification pharmaceuticals (e.g. via return shipment or to a nearby bricks-and-mortar location) and effecting the appropriate settlement between the involved parties. The Intelligent Label Processing System establishes a robust mechanism for data collection and verification by interested parties in the process.

The current custodian of the good is able to use the intelligent label to direct processes, which may in some cases be the consumer, and in others may be a shipper or other third party. For example, an intelligent label that has a simple message, for example, a red 'dot', can direct a party that the associated good take an exceptional process path while all others are processed normally. The local custodian can communicate the status of the good and the existence of exception events by a variety of means. In one instantiation, the custodian takes a photo of the intelligent label including the message, the red dot, with a mobile phone camera and transmits it to other parities in the supply chain.

All parties in the supply chain, both local and remote, can use these messages to validate events and to build business rules based around the events' occurrence. In this regard, it is important that the electro-optic display is preferably permanent and irreversible in order that all parties in the supply chain are able to authenticate the event. Having a permanent or near permanent and irreversible electro-optic display is desirable as it reduces or avoids accidental and intentional modification of messages and enables them to be verified after the event. These messages can also be coupled with other private data that are electronically accessible to a party in possession of the intelligent label through, for example, RFID protocols. In addition, these messages can be coupled with other public information printed on the label or the good, such as a serial number, customer identification number, sales order number or ship time/date. Any of these messages and associated information can be made available to other parties in the supply chain prior to or during the distribution process. And they can support further levels of authentication and provide additional contextual information about the event. Secure and robust processes can be built that depend on the coupling of these messages and other information on the label (including some unknown and inaccessible by the local custodian) and traditional supply chain transaction information.

The establishment of a verifiable chronology for a good is key in the development of these processes. The intelligent label can be used to establish a timeframe for events and changes of custody of interest surrounding a good. Events that are tracked by the intelligent label beyond this point can be made with respect to that point in time. In some cases this time can be synchronized with absolute time, but in many cases this synchronization is not required.

Two Surface Activation and Message Generally

Described here is a construction for an electro-optic display that can be permanently and irreversible set in a first activation to show a first message, and later, if the underlying information is determined to be incorrect or incomplete, the message can be changed, supplemented or obliterated. One example construction uses two opposite sides of a transparent electro-optic layer for the activations. That is, the first message is first set into a first message surface of the electro-optic layer, and during the second activation, a second message is set into the second message surface of the electro-optical layer so that the perception of the first message is altered or obscured. Doing so enables trusted and verified parties to control the message at any point during its life, and provide up to date, accurate information. In one particular example, the intelligent label is constructed to allow for multiple activations and thus multiple messages. In this way, a first activation can set a first message, and later if that message proves to be false, misleading, or incorrect, then one or more additional activations may be set that obscure or change the first message.

As described above, the preferred embodiment of the intelligent label includes a novel permanent and irreversible electrochromic material that can be deposited or printed on or along-side each electrodes used to activate and thereby set messages on the message services of the electro-optic display and that consist for example of the segments of a 7-segment display. And further, that use technology applicable to many applications utilizing thin-film and flex-circuit designs. When energized the preferred electrochromic material undergoes a permanent irreversible change in color and can thus be used for messages that can change dependent on a prescribed set of conditions being met. In use a control circuit energizes or activates elements of the display as required by the application so that the display shows appropriate messages. The form of the message can be simple such as an icon or symbol; or it may be complex such as one or more numeric or alpha characters. Sometimes, the messages might be inaccurate due to changes in circumstances, information, or standards to which product viability is measured. In these instances, it would be of great importance to change the messages to alarm, update or inform the consumer, wholesaler, or possessor of the good that the good is no longer suitable for use or consumption. Therefore, it is desirable to create an irreversible label with two message surfaces, one to display an initially correct message, and another layer to warn if the messages is no longer correct, or in some cases to update, obscure, or alter the message.

Such an additional separately activated message may be used to inform the user that the information being displayed is incorrect or should not be relied upon, or to provide updated information. A scenario for use in the pharmaceutical industry, for example, would be prescriptions or test drugs that have a specific "use by" date on them. If this date is later deemed to be inaccurate, the intelligent label can, using an additional message surface, inform the user that the drugs should not be taken. Two example constructions for two-surface activation will be described for illustrative purposes.

In one construction, a two-surface electro-optic display uses a single transparent electro-optic layer that is sandwiched between two electrode layers. These three layers are supported on a substrate, and they may be encapsulated with a protective coating. The substrate may be provided particularly as the base for depositing the electrode and electro-optic layers for the display device, or alternatively, may be components of the intelligent label. The first, or bottom electrode layer, which may be transparent or opaque, has its surface facing upward toward the electro-optic layer. The first electrode layer has both positive and ground conductors in an interdigitated or patterned arrangement that, using intelligent label electronics, are used to set a permanent and irreversible first message in the bottom message surface of the electro-optic layer. The second or top electrode layer, which is transparent, is downward facing into the electro-optic layer. The second electrode layer also has both positive and ground conductors in an interdigitated or patterned arrangement that, using intelligent label electronics, are used to set a permanent and irreversible second message in the top message surface of the electro-optic layer that changes, supplements or obliterates the first message. Importantly, the two electrode layers are activated independently of each other. It will be understood that many variations are possible as to the specific electrode design and placement, which can be defined according to application specific requirements.

In a second construction, a two-surface electro-optic display again uses a single electro-optic layer, but its two associated electrode layers each only use one electrode. In this construction, the electrode facing the bottom message surface is in a pattern to provide a first message, and the top electrode, which is transparent, is in a pattern to provide a second message that obliterates the first message. When the intelligent label determines to set the first message, the electronics in the intelligent label apply a comparatively high, positive voltage on the bottom electrode and then apply a lower, positive voltage on the top electrode. This allows the first message to be set only into the bottom message surface of the electro-optic layer, and does not materially affect the top message surface. Later, when the first message is to be obscured or changed, the electronics in the intelligent label apply a relatively high, positive voltage on the top electrode followed by a lower, positive voltage on the bottom electrode. This allows the second message to be set into the top surface of the electro-optic material, thereby interfering with or changing the viewable or readable perception of the first message.

Two Surface Message Activation Using Two or More Electrode Pairs

Referring now to FIG. 1, a partial side, cross sectional view 100 of selected active elements for a two-surface 7-segment display are shown. Here, the bottom substrate 106 can be any of a number of different materials, but most commonly will be a flexible plastic or polymer that can be used in a number of manners. This substrate 106 may be particularly provided to function as the support of the display device, or may be a substrate associated with, for example, an intelligent label. On the bottom substrate 106 is the first electrode layer 104, which can be a transparent conductor such as ITO or an opaque conductor such as a metal, which has been patterned to allow the presentation of the 7-segment display. In one construction, each of the 7 segments is an interdigitated pattern of positive and negative electrodes. A transparent electro-optic layer 105 is on top of the bottom electrode 104. The specific electrochromic material of the electro-optic layer 105 is made to be activateable in a way that its color or quality change is permanent and irreversible. Most often this electro-optic layer 105 will be transparent or near transparent so that the viewer can discern the message or character generated by the first electrode layer 104. Accordingly, it is the first electrode layer 104 that is activated by the intelligent label electronics that causes the bottom message surface of the electro-optic layer 105 to have a message permanently and irreversibly set.

A second transparent electrode layer 101, such as ITO, is on top of the electro-optic layer 105. The second electrode layer 101 has been patterned to allow the setting of an obscuring message into the top message surface of the electro-optic layer 105. In one construction, the obscuring pattern is an interdigitated pattern of positive and negative electrodes, and can be of one or multiple segments. In this way, when the second message is set by the second electrode layer the first message set by the first electrode layer is obscured so that its perceptibility or meaning is substantially altered, reduced or made meaningless. Accordingly, it is the second electrode layer 101 that is activated by the intelligent label electronics that causes the top message surface of the electro-optic layer 105 to have an obscuring message permanently and irreversibly set. The pattern of the second electrode layer 101 is described as being an obscuring pattern, but it will be understood that other patterns may be used to create other messages. For example, the second activation may add additional color, symbols, or lines that when viewed in combination with the first message, provide a new updated or corrected combined message.

Figure 2:
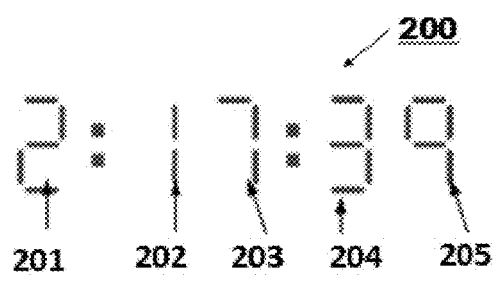
FIG. 2 is a block diagram of a seven-segment display layer in accordance with the present invention.

Referring now to FIG. 2, it is shown that a certain message 200 can be activated during the first electrode layer 104 activation, which permanently and irreversibly sets the message ("2:17:39") into the bottom message surface of the electro-optic layer, such as electro-optic layer 105 of FIG. 1. This is accomplished by the programmed label electronics sending electrical signals to electrodes in the first electrode layer, such as electrode layer 104 of FIG. 1, which in turn energize of activate the appropriate individual segments (pixels) of the electro-optic layer. In FIG. 2, each of the symbols 201-205 is constructed as a separate 7-segment character. Once activated, the message ("2:17:39") is set or fixed into the electrochromic material of the electro-optic layer and is irreversible and permanent, allowing the customer to rely on the message being displayed. The message is thus set into the bottom message surface of the electro-optic layer 105. If at a later time, it is determined that the information underlying the first message is no longer correct, then the second electrode layer 101 of the intelligent label is activated to change or obscure the first message by setting a permanent and irreversible pattern message into the top message surface of the electro-optic layer 105. The determination of when to active the second, the obliteration, pattern can be made remotely and wirelessly communicated to the intelligent label using a network system and RFID communication, or in some cases the determination can be made within the intelligent label itself responsive to timers or sensors.

Figure 3:
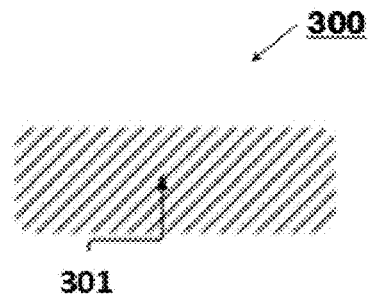
FIG. 3 is a block diagram of an obscuring pattern in accordance with the present invention.

FIG. 3 is a representation 300 of one possible obliteration pattern 301 that can be activated in the second electrode layer to create a message that the previous message, the first message is no longer accurate or reliable. In this particular design, the first message is no longer readable because the pattern or segments of the second message in the second message layer are diagonally overlapping the original, first message. Here, the bottom message surface of the electro-optic layer 105 has been activated by a trusted party with correct information at the time of initial activation. At some point in time between the initial activation and the time of FIG. 3, a trusted party has deemed the first message inaccurate. When the first message is deemed to be inaccurate, a trusted and verified party may alter the first message by activating the second electrode layer 101 to show the second message, the obliteration pattern 301, on the top message surface of the electro-optic layer 105. In this particular design, electrodes are arranged in the second electrode layer in a diagonal fashion. Before the first activation, the electro-optic layer is transparent as are the diagonal electrodes in the second electrode layer so that after the first activation, the first message may clearly be read or viewed from the top (as indicated by the "viewing perspective" arrow). After activation of the second electrode layer 101, the top message surface of the irreversible electro-optic layer 105 is set and the second message of a diagonal pattern 301 informs the consumer (or machine reader) that the product is not safe for use. It should be made clear to users of the intelligent label that a message showing of a diagonal pattern such as this means that the product or good is not suitable for use. The second message surface is activated in a similar fashion to the first message service. The second electrode layer 101 may be more simplistic than the 7-segment arrangement in that it can mean either entirely "on" or "off" "use" or "don't use". There may be no individual segments to either activate while others are not active, or keep inactive when all others are active. Alternately, the pattern to be activated can be constructed of multiple segments to control power usage, or to provide partial obliteration. It will be understood that many alternatives are possible for the message pattern of the second layer within the scope of this disclosure.

In one other example, the second electrode layer does not obscure the bottom message, but changes its perceptible content. For example, the bottom message surface of the electro-optic layer may be activated first to display a set of horizontal dashes. At a later time, the top message surface of the electro-optic layer may be activated to add a vertical line. When viewed or read from the top, the resulting message is one or more "+" signs. In a similar way, the bottom message surface can be set to a particular color, and then later the top message surface can be set to another color. When viewed from the top, the perceptible color would be the combination of both the top message surface and bottom message surface colors. In one example, the electro-optic layer consists of an electrochromic material that can be changed to more than one color depending on the specific signal applied during activation. For example, the electrochromic material may transition to a first color at a very high voltage, but may transition to a different color at a lower voltage. It will be understood that other signal characteristics such as length of application and waveform type may also affect the final color. Using the color control capability of the electrochromic material, a voltage may be selected the first activation to set a first color on the first message surface. Then, at a later time, the second message surface is activated using a different signal voltage, which sets a different color into the second surface. In this way, the final color that is viewed is a combination of the two message colors.

In one specific example, each surface of the electro-optic layer has a pair of associated interdigitated electrodes. At a first time, a conditioning signal at a moderate voltage, such as 3 volts, is applied for several seconds. Then, the polarity is reversed and a smaller, for example 1 volt, setting signal is applied. This sets the first surface to color, such as red. It will be understood the specific color can be adjusted by the voltages, timings, and material compositions. At a later time, the second surface can be colored by activating the electrodes at a higher voltage, such as 7 volts, which sets the second surface to a different color, such as blue.

Figure 4:
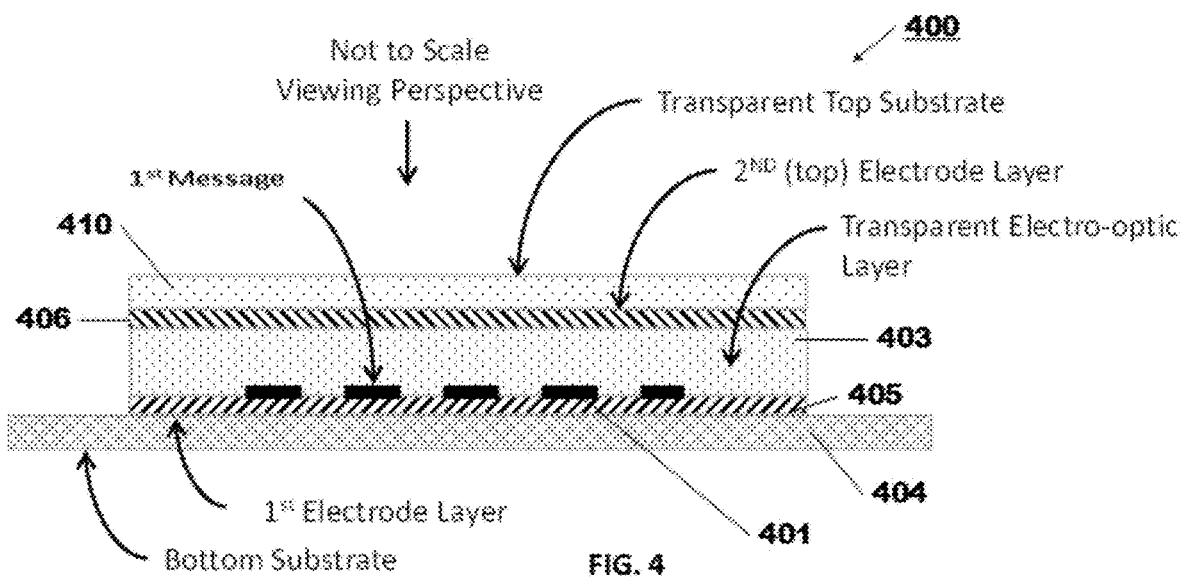
FIG. 4 is a block diagram of a side view of a display device in accordance with the present invention.

FIG. 4 provides a side view of a portion of an intelligent label 400 using the two-surface display from FIG. 1, FIG. 2, and FIG. 3. The intelligent label 400 has a bottom substrate 404 with a first electrode layer 405 that is arranged to implement a 7-segment electro-optic display. It will be understood that electrical conductors are provided (not shown) that couple the segments to the intelligent label's electronics and power. Over the first electrode layer 405 is a layer of electro-optic material 403. The intelligent label 400 also has a top substrate 410 with a second electrode layer 406 that is arranged to implement an obscuring pattern in the top message surface of electro-optic layer 403. During the first activation (FIG. 2), segments of the first, or bottom electrode layer 405 are selectively activated to permanently set a message into the bottom message surface of the electro-optic layer 403 that is human or machine readable. The message is viewable to the user because the electro-optic layer 403 and the top substrate 410 and second or top electrode layer 406 are transparent. When power is applied to the selected segments, the electrochromic material of the electro-optic layer on or adjacent to the segments will be permanently transitioned to a new color or transparency state. Non-selected segments may have their "select" lines "floating", that is connected to an output driver capable of a high-impedance state, commonly known as a tri-state condition. Alternatively, non-selected segments may have all segment electrodes and the common counter-electrode set to a "high" level, i.e. the "activation voltage". In this condition no segments will be activated to the colored state since there is no voltage difference across the electro-optic material.

Figure 5:
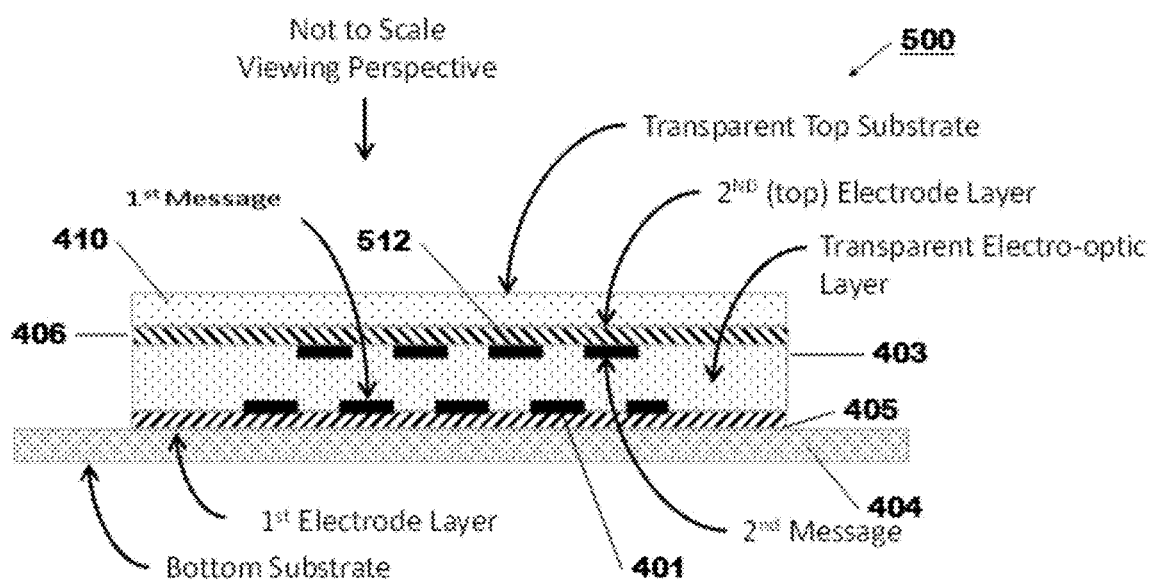
FIG. 5 is a block diagram of a side view of a display device in accordance with the present invention.

FIG. 5 further provides the same view as shown in FIG. 4, but is illustrated to also show a message 512 in the top message surface of the electro-optic layer 403 after the second or top electrode layer 406 is activated. It should be understood that the first message 401 in the bottom message surface of the electro-optic layer 403, is irreversible, so it does not cease to display the image it has been set to by the intelligent label circuits. The second message 512 is also irreversible, but, when it is set into the top message surface of the electro-optic layer 403, the first message set into the bottom surface of the electro-optic layer 403 by first electrode layer 405 is no longer readable (as in FIG. 3). Since the second electrode layer 406 in this example is patterned as a dense crosshatch, as is the pattern of the top surface of the electro-optic layer once activated, the first, bottom message is nearly entirely obscured. It will be understood that a more or less dense pattern may be used according to application needs, as well as power and time availability. Alternatively, the second message can be used to modify or change the perception of the first message, as described earlier.

Figure 6:
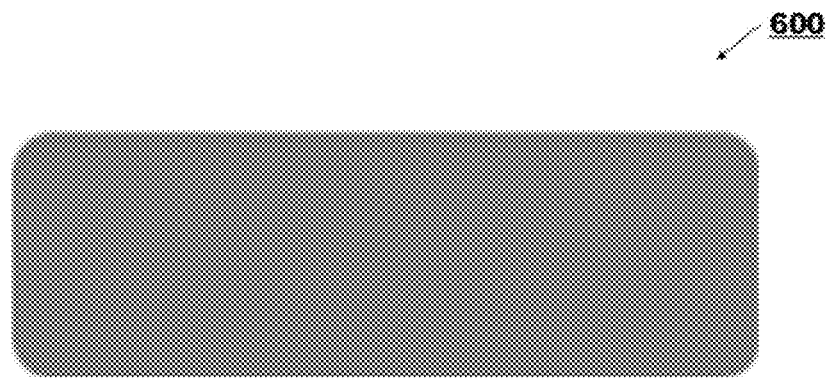
FIG. 6 is a block diagram an obscuring pattern in accordance with the present invention.
Figure 7:
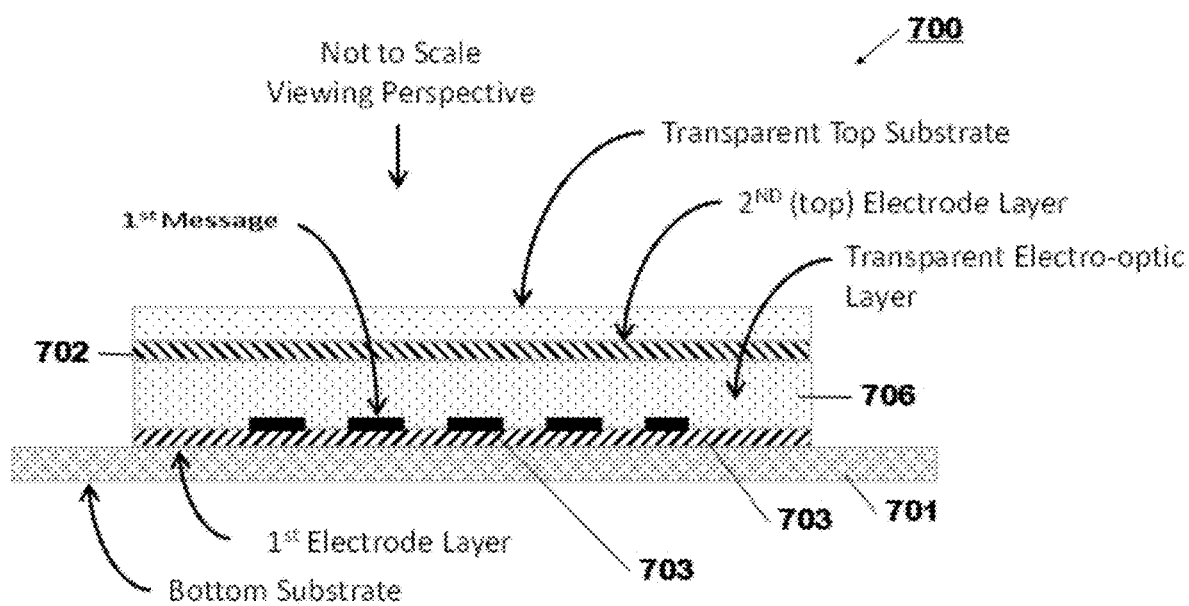
FIG. 7 is a block diagram of a side view of a display device in accordance with the present invention.

In an alternate design, it may be essential for the entire first or bottom message to be unreadable by any practical means. In a similar fashion to the two-surface display, this type of device will display a first message that is critical to the use of the intelligent label. However after a certain point they can no longer be perceived or interpreted. For instance, pharmaceuticals that are discovered to have expired before the date or time displayed represent a very important change in information. In this critical use, the intelligent label must reliably prevent the first message being displayed on the intelligent label from being read or interpreted by anyone or anything. To achieve that outcome the second electrode layer (FIG. 6) in this example is configured so that upon activation, a fully solid shape 600 that covers or blocks the perceptibility of the first message is set into the top message surface of the electro-optic layer. The first message therefore becomes completely unreadable because it is completely covered by the second or top message, a solid shape, and is no longer perceptible by the human eye, nor by most technology designed to read or scan for codes such as those that might be messages displayed by the intelligent label.

Figures 8, 9, 10:
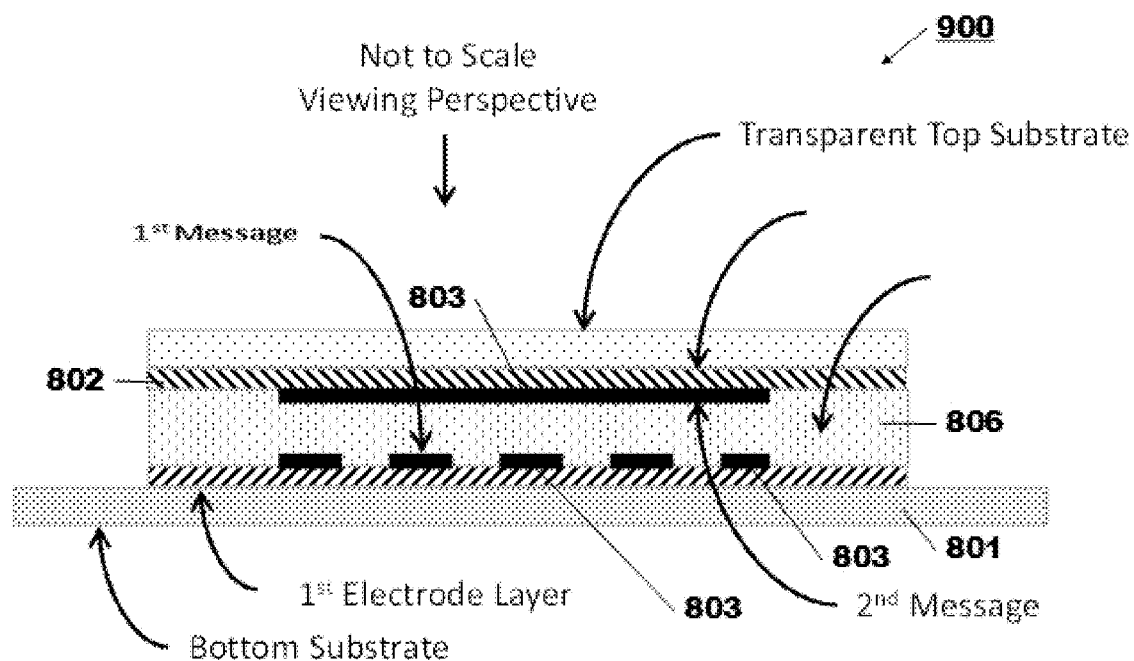
FIG. 8 is a block diagram of a side view of a display device in accordance with the present invention.
FIG. 9 is an illustration of an informational message using a seven-segment display.
FIG. 10 is an example of modifying the information message of FIG. 10 to be nonsensical.

In another example, the first or bottom electrode layer has electrodes arranged in a pattern, such as for making 7-segment characters. Upon command, a first message can be set permanently onto first message surface, such as the message 900 "2:17:39" as shown in FIG. 9. The second electrode layer has electrodes arranged in a complementary pattern to, and aligned with, those of the first electrode layer. In this way, a second message set on the second message surface can alter, or makes nonsensical, the first message on the first message surface layer. By way of example, FIG. 10 shows the display of FIG. 9 where the second activation has filled in the 7-segment display to show the nonsensical message 1000 "8:88:88." It will be understood that many other message patterns could be used on the second activation.

Figure 11:
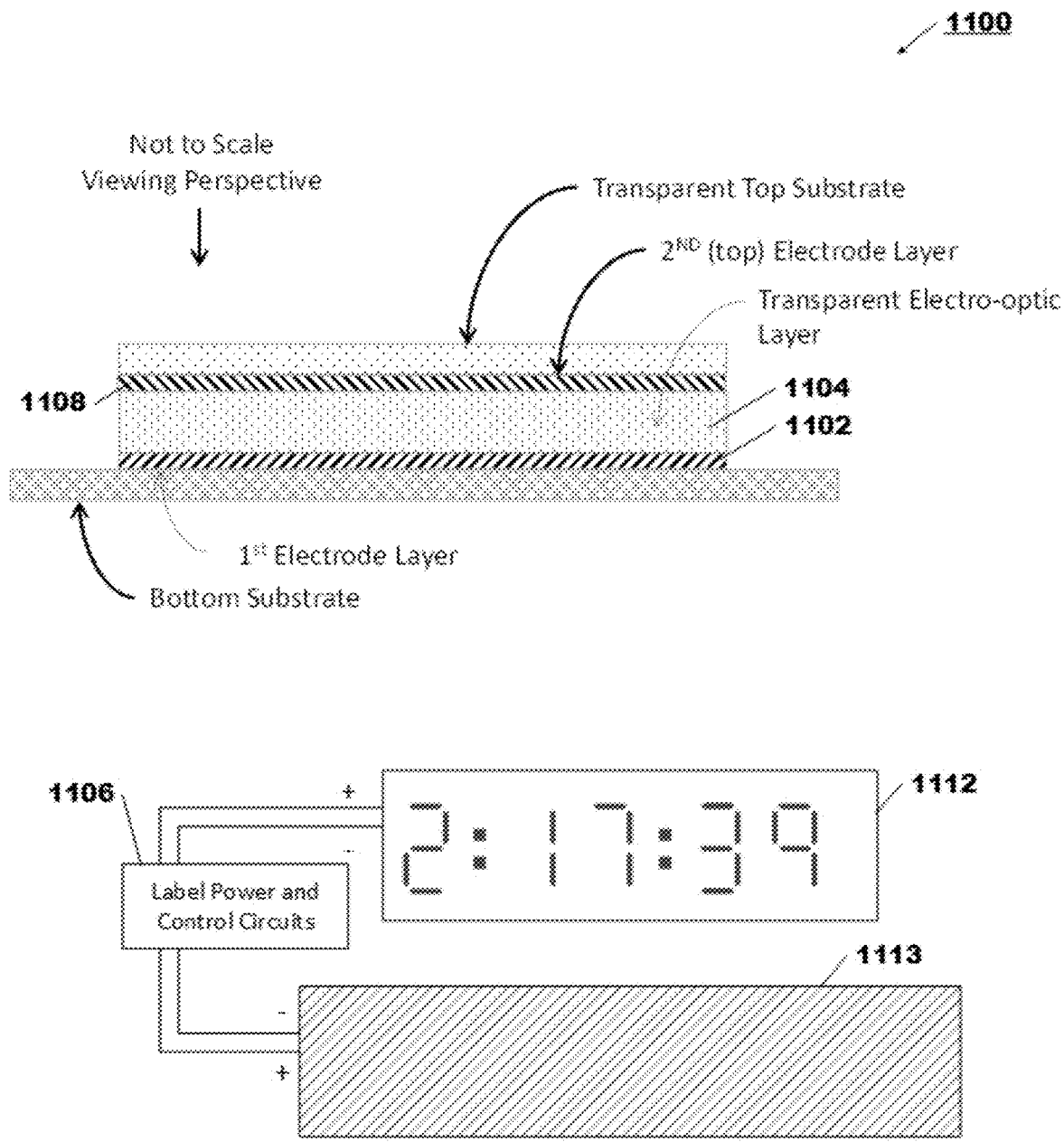
FIG. 11 is a block diagram of a side view of a display device in accordance with the present invention.

In another example illustrated in FIG. 11, the electrodes in both the first 1102 (bottom) and second 1108 (top) electrodes layers are interdigitated. That is, each electrode layer 1102 and 1108 has at least one positive electrode and one ground electrode, configured to form a pattern that when activated, set permanently and irreversibly a first and second message respectively in the bottom message surface and the top message surface of the electro-optic layer 1104. In this way, the label power and control circuits 1106 can effect a first message 1112 to be set into the bottom message surface of the electro-optic layer 1104. The top electrode layer 1108 has interdigitated electrodes configured in a crosshatch or other obliterating pattern 1113. That is, top electrode layers 1108 has both a positive electrode and a ground electrode, and when activated, permanently and irreversibly set a second message 1113 on the second, top message surface of the electro-optic layer 1104. It will be understood that as previously described, many other messages can be created this way.

Dual Message Activation Using One Electrode Pair

Figure 12:
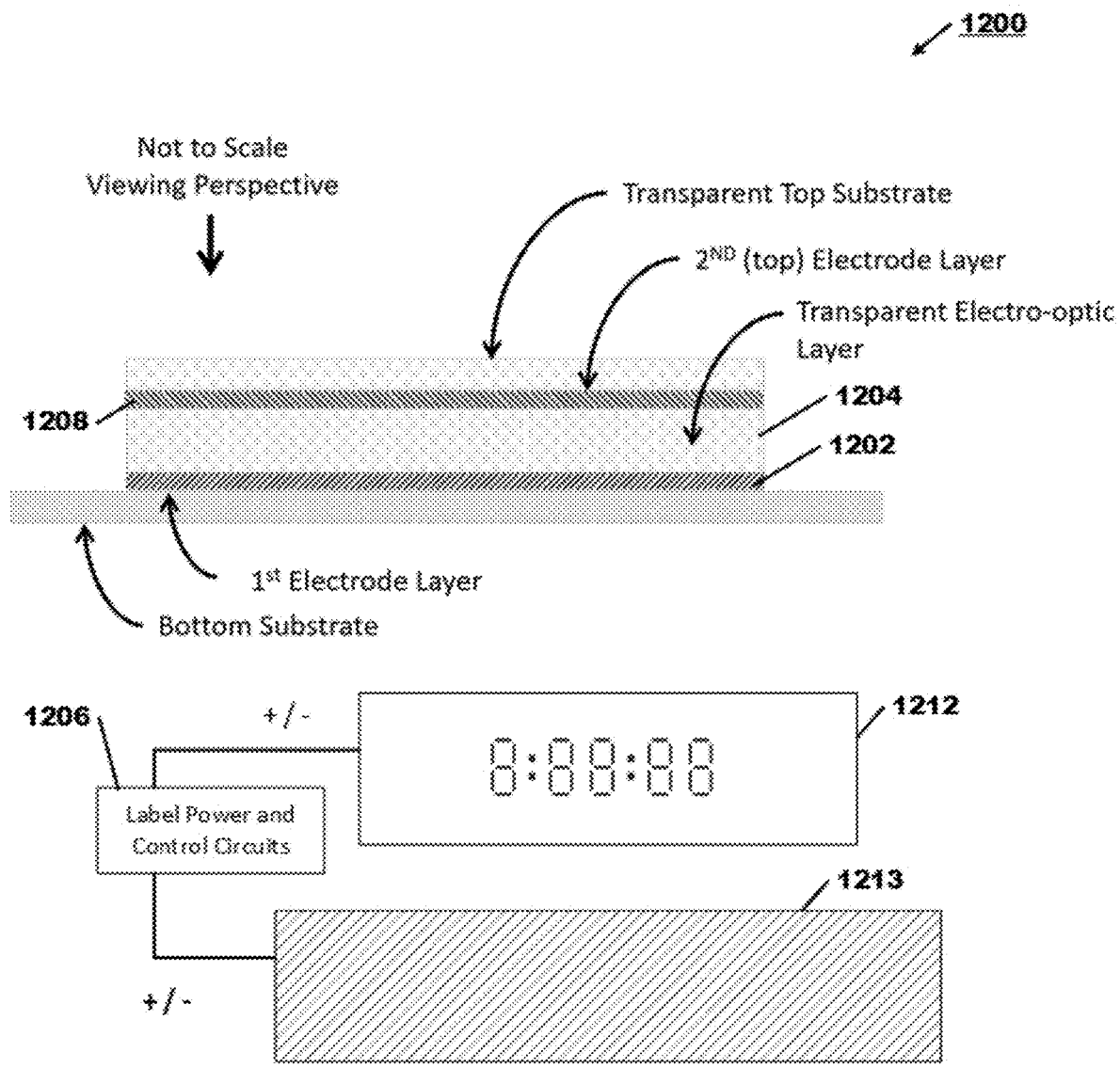
FIG. 12 is a block diagram of a side view of a display device in accordance with the present invention.
Figure 13:
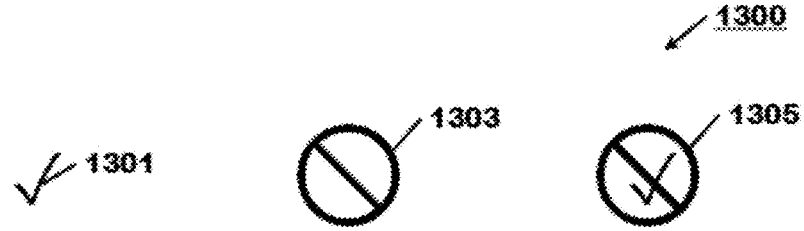
FIG. 13 shows example messages.

In a particular embodiment shown in FIG. 12, a portion of an intelligent label 1200 may be constructed in using a simple three-layer electro-optic display that uses only one electrode pair. Referring still to FIG. 1s, a layer of electro-optic material 1204 that comprises the electro-optic layer is sandwiched between a bottom electrode layer 1202 and a top electrode layer 1208. The bottom electrode layer 1202 is constructed to form a pattern in the bottom message surface of the electro-optic layer with a single electrode. As illustrated in FIG. 13, the bottom pattern 1301, and thus the bottom message, could be a simple, single symbol such as check mark 1301 that shows that an item has been inspected and is ready for use. The top electrode 1208 is constructed to form a second pattern 1303 into the top message surface of the electro-optic layer also using a single electrode. The top electrode layer 1208 in this case being transparent. As illustrated in FIG. 13 the top pattern 1303, and thus the resultant top message, could also be a simple, single symbol such as an "Ø" positioned over the bottom message 1301. When activated the compound message 1305 would show that the item is no longer to be used. Alternatively, the second pattern could supplement or obscure the first pattern 1301 as previously discussed.

Compared to certain of the examples discussed earlier, this particular embodiment may be easier to design and manufacture, and may simplify the control circuits. For example, the bottom electrode 1202 may be a single driveline from the label power and control circuits 1206. Under control of the control circuit 1206, the bottom electrode 1202 driveline may be either positive or negative, and may be set at different voltages. In a similar manner, the top electrode 1208 drive line may be either positive or negative, and may be set at different voltages. The polarity, timing, and voltage levels are set by the control circuitry 1206 according to which of the top or bottom surface of the electro-optic material 1204 is to be set.

Figure 14:
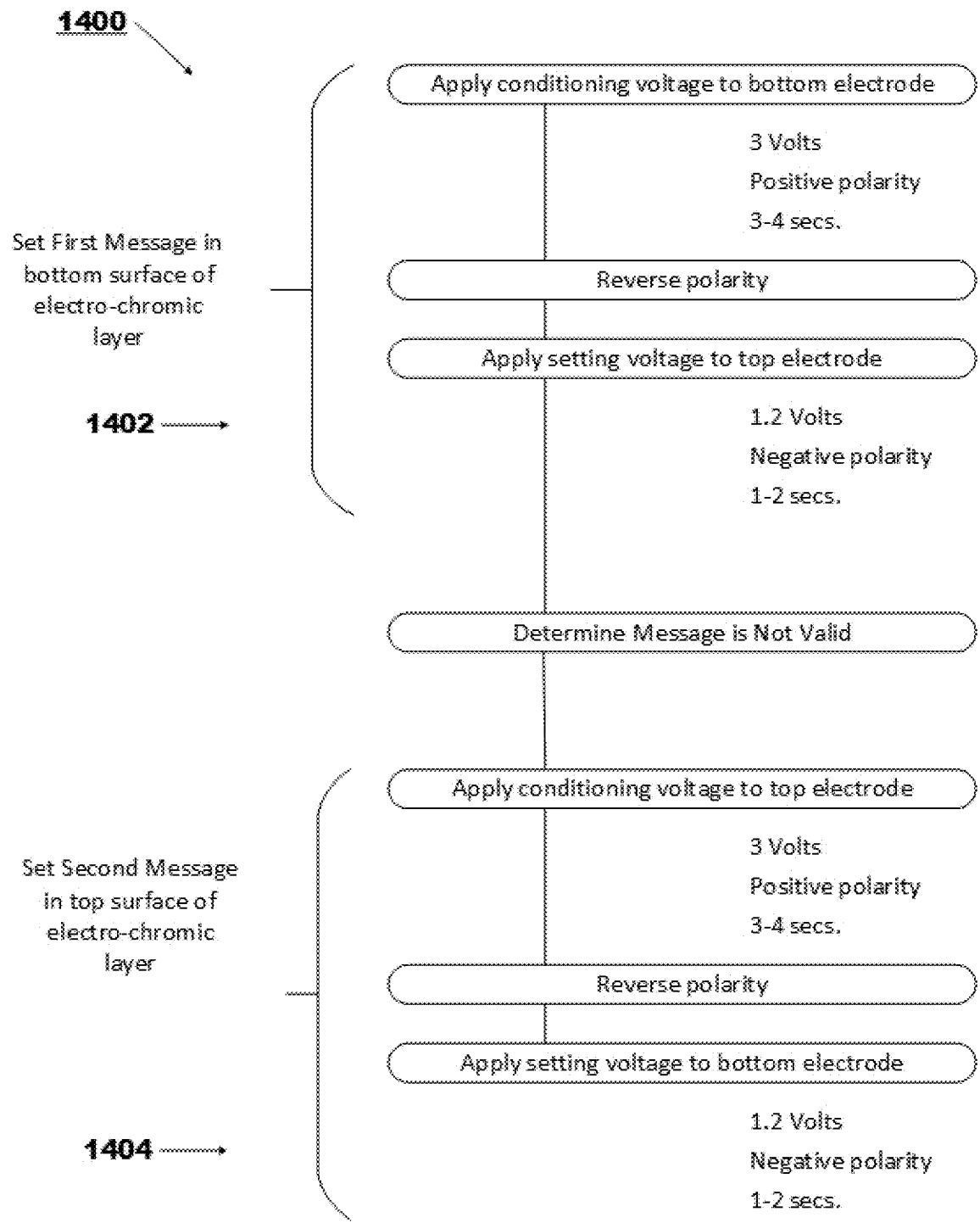
FIG. 14 is a flow diagram of a process to set and later obscure or change an information message on a display device in accordance with the present invention.

Referring now to FIGS. 12 and 14, an illustrative method 1400 of using the display device of FIG. 12 is shown. It will be understood that the particular times, polarities, and voltages are selected according to the particular electro-optic material used, and its particular physical construction (such as thickness).

The intelligent label's control circuit 1206 determines that a first message should be set 1402 responsive to either an external message received from a network or remote system, or internal stimuli such as timers or an environmental sensors. Once the intelligent label control circuit 1206 determines to set the first (bottom) message, it uses local power to apply a first conditioning signal, which is provided as a first voltage to the bottom electrode 1208, which is adjacent to the bottom message surface of the electro-optic layer 1204. This conditioning voltage may be a relatively high, for example 3 volts, and applied for a relatively long period of time, for example 3 to 4 seconds. It will be appreciated that other voltages and times may be used, and that the conditioning voltage may be applied in bursts, ramps, pulses, or other such waveforms or variations. After the first conditioning signal is completed, the control circuitry 1206 reverses the polarity, and applies a first setting signal, which is provided as at a second voltage to the top electrode 1208, which sets and permanently fixes the bottom message into the bottom surface of the electro-optic material 1204. This setting voltage is typically at a lower voltage than the conditioning voltage, such as 1.2 volts, and is applied for a shorter period of time, such as 1-2 seconds. It will be appreciated that other voltages and times may be used, and that the setting voltage may be applied in bursts, ramps, pulses, or other such waveforms or variations. This setting voltage is selected to be low enough and short enough that it sufficiently fixes the bottom message in the bottom message surface of the electro-optic layer 1204, but has little if any effect on the top message surface of electro-optic layer 1204. The message set into the bottom surface of the electro-optic material is now fixed, permanent, and irreversible, thereby providing valuable visual information to a viewer or reader of the intelligent label.

At a later time, the intelligent label may be made aware that the bottom message is no longer valid or needs to be updated or corrected. This determination can be made remotely and communicated to the intelligent label control circuits 1206, or the intelligent label control circuits 1206 may make that determination responsive to a timer or environmental sensor. Accordingly, it is important that a new, second or top message is generated that either obscures the current, bottom message or in combination with the current message, creates a third, corrected or updated message.

To set a top message 1404, the process described above is basically reversed. Once the label control circuitry 1206 determines to fix a message into the electro-optic layer 1204, it uses local power to apply a second conditioning voltage to the top electrode 1208, which is adjacent to the top message surface of the electro-optic layer 1204. This voltage may be a relatively high, for example 3 volts, and applied for a relatively long period of time, for example 3-4 seconds. It will be appreciated that other voltages and times may be used, and that the second conditioning voltage may be applied in bursts, ramps, pulses, or other such waveforms or variations. After the second conditioning voltage is completed, the control circuitry 1206 reverses the polarity, and applies a second setting voltage to the bottom electrode 1202, which sets and permanently fixes the second (top) message into the top message surface of the electro-optic layer 1204. This setting voltage is typically at a lower voltage, such as 1.2 volts, and is applied for a shorter period of time, such as 1-2 seconds. It will be appreciated that other voltages and times may be used, and that the setting voltage may be applied in bursts, ramps, pulses, or other such waveforms or variations. The change or obliteration pattern set in the top message surface of the electro-optic layer is now fixed, permanent, and irreversible, thereby alters the combined message that can be viewed or read. If the second activation used an obscuring pattern, then the second activation prevents, hinders or discourages a viewer or reader from using the underlying first (bottom) message. If the second activation was a supplementing or altering pattern, than a new message, which is the combination of the upper and lower patterns, is now viewable and readable.

In an extension to this activation process, the application of a different voltage on the first surface as compared to the second surface can result in each surface being fixed at a different color. In a specific example, the bottom conditioning and setting voltages remain as described above with reference to FIG. 12, but the top conditioning signal is applied at a higher voltage, such as 7 volts. In this way, a first color is set on the bottom surface, and a second color is set on the top surface. In this way, a resulting message can be the perceived combination of the bottom and top colors.

In a slight modification to the process and device described above, to colors may be set into a single surface using the general activation voltage described above. For example, a lower activation voltage may be applied to a portion of a surface at a first time, setting a pattern or symbol to a first color, and at a second time, a higher activation voltage can be applied to a different portion of the surface, setting a pattern or a symbol in that area to a second color. In yet another modification, a pattern or patterns can be provided by a set of segments on a single surface, with each of the segments comprising an interdigitated electrode pair. In this way, each segment can be color to a first color with application of a lower activation voltage, or to a second color with the application of a higher activation voltage. In this way, all the segments could be set to a first color, all to a second color, or some to the first color and some to the second color.

In certain constructions, and depending in part on the composition of the electro-optic layer, desired speed of transition, available power, and the desired persistence of the message, alternative activation methods may be advantageously used. Using the single pair, dual layer electrode construction such as that described above, a first, bottom message and a second, top message may be fixed, using a first signal, first voltage and a second signal, second voltage. The first signal, comprising a first voltage may be applied to the bottom electrode generating a first, bottom message. Once the first voltage is completed the message may exhibit less persistence than when followed immediately by a setting signal, setting voltage or it may naturally transition to longer persistence or permanence. Subsequent to the first signal, first voltage being completed the polarity may be reversed and a second signal, second voltage applied to the second, top, message surface of the electro-optic layer. This second signal, second voltage would generate a second, top message. And importantly, it would also function as a first setting signal, first setting voltage, and fix the first message permanently and irreversibly. It is to be understood that different electrode constructions and activation signals can be used to advantageously depending on the desired function and performance of the intelligent label.

Two Sided Display

Figure 15:
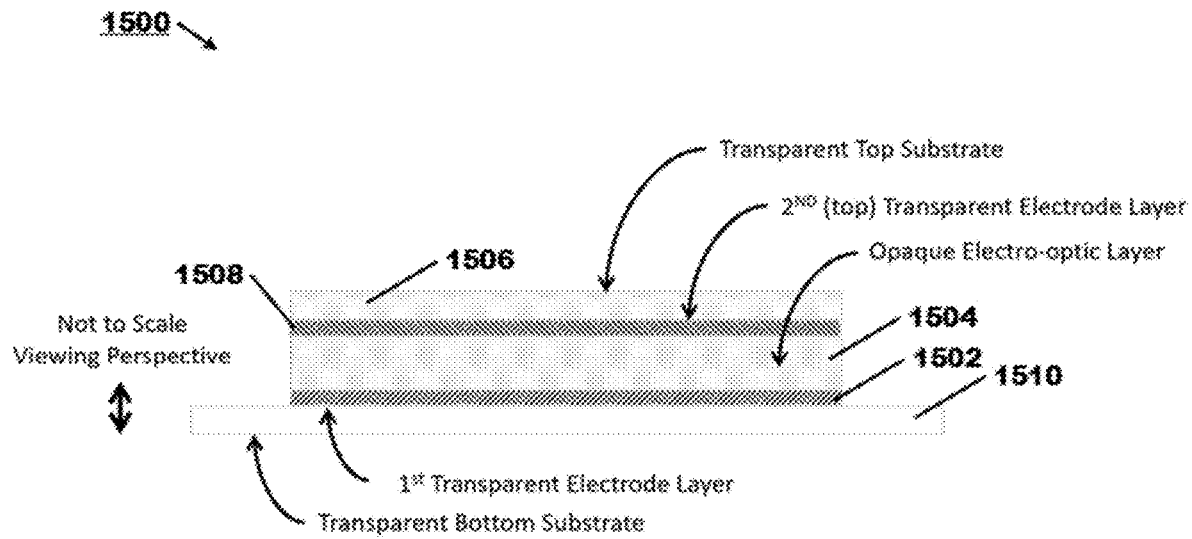
FIG. 15 is a block diagram of a side view of a display device in accordance with the present invention.

As illustrated in FIG. 15 an electro-optic display 1500 may be constructed with an opaque electro-optic layer 1504, a first, bottom transparent electrode layer 1502, a second, top transparent electrode layer 1508, a transparent bottom substrate 1510 and a transparent top substrate 1506. Once activated, a first message on the first, bottom, message surface of the electro-optic layer 1504 can on be seen from one viewing position, and a second message on the second, top message surface of the electro-optic layer 1504 can be seen from an opposite viewing position. In this way, a two-sided label, tag windshield sticker or window display etc. can be constructed, with each message independently controlled. It will be appreciated that this construction can use different combinations of electrode configurations such as interdigitated or single electrodes as set forth above. A similar construction using a transparent electro-optic layer can also be used to create compound messages that can be viewed from both viewing perspectives.

Two or More Electro-Optic Layers

Figure 16:
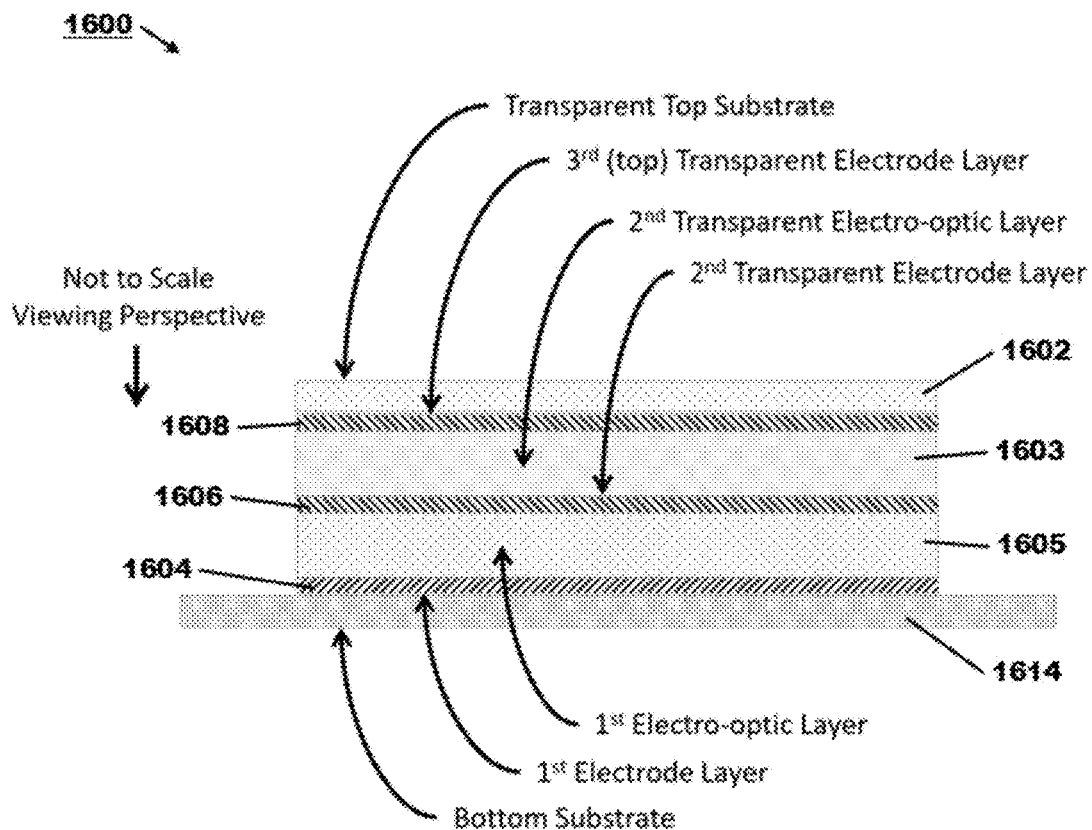
FIG. 16 is a block diagram of a side view of a display device in accordance with the present invention.

Electro-optic displays can also be constructed with more than on electro-optic layer and corresponding electrode layers as appropriate. FIG. 16 illustrates an electro-optic display 1600 comprising two electro-optic layers (1603 & 1605) and three electrode layers (1604, 1606, &1608). Combined, the electro-optic device would have a total of four message surfaces: one on each side (top and bottom) of each electro-optic layer.

An example of the single signal activation method describe above follows. A first voltage signal is applied to the first (bottom) electrode layer 1604 using the middle electrode layer 1606 as a ground. This arrangement would activate the first (bottom) message surface of the first electro-optic layer 1605 and create a first message. A second signal, applied to the middle electrode 1606 using the first (bottom) electrode layer 1604 as a ground, would set a second message on the top message surface of the first electro-optic layer 1605. A third signal, applied to the second (middle) electrode 1606 using the third (top) electrode layer 1608 as a ground, would set a third message on the bottom message surface of the second electro-optic layer 1611. A fourth signal applied to the third (top) electrode 1608 using the middle electrode 1606 as a ground, would set a fourth message on the top message surface of the second electro-optic layer 1611. The electro-optic layers (1603 & 1603), electrode layers (1604, 1606, &1608) and substrates (1602 and 1614) are advantageously transparent or near transparent, or opaque depending on the desired functions, viewing direction, and particular application for the electro-optic display or intelligent label.

Figure 17:
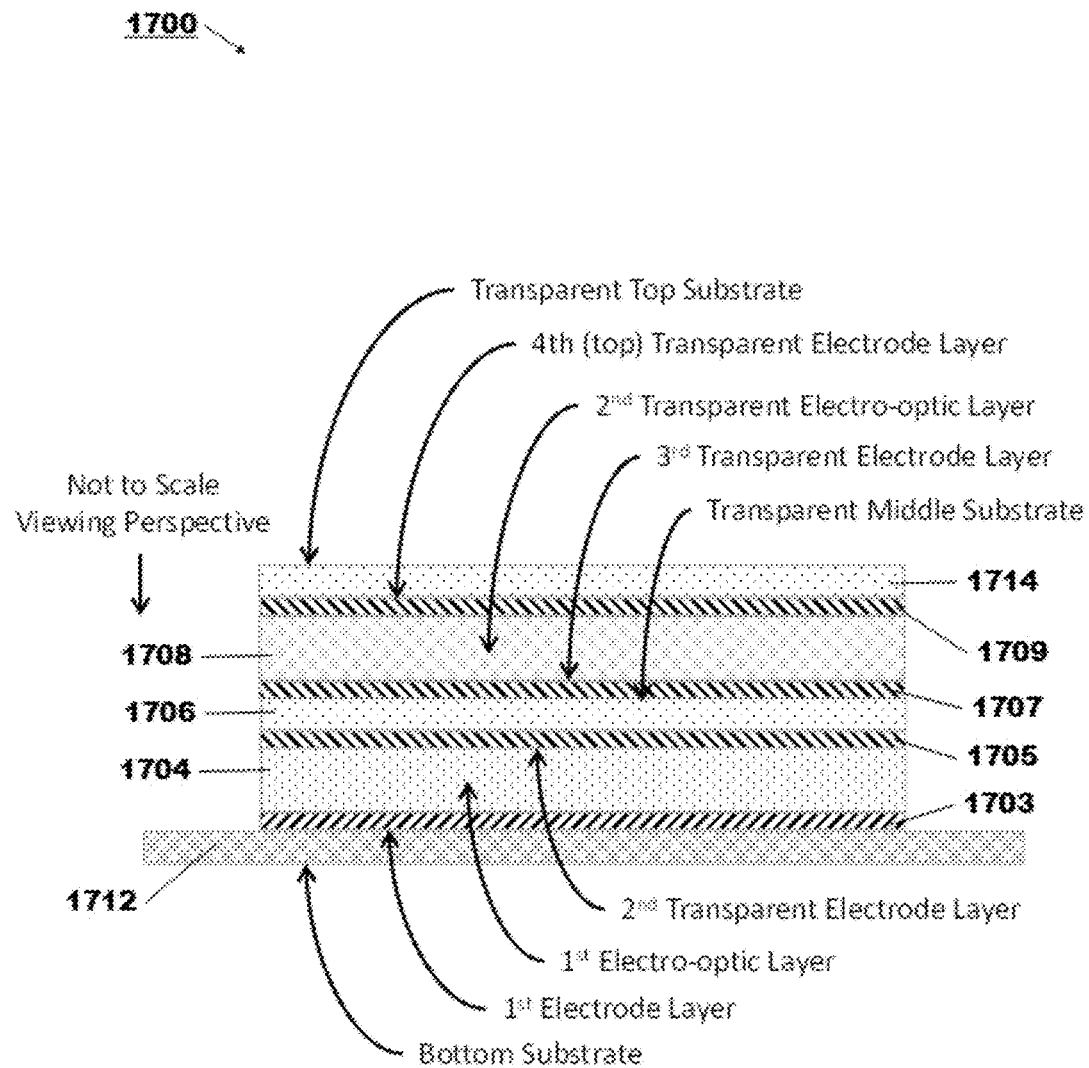
FIG. 17 is a block diagram of a side view of a display device in accordance with the present invention.

FIG. 17 illustrates an alternative four surface electro-optic display 1700 constructed using a middle, transparent substrate 1706 with an additional electrode layer. As in the previous example the electro-optic layers (1704, 1706 & 1708), electrode layers (1703, 1705, 1707 & 1709) and substrates (1712 and 1714) are advantageously transparent or near transparent, or opaque While particular preferred and alternative embodiments of the present intention have been disclosed, it will be appreciated that many various modifications and extensions of the above described technology may be implemented using the teaching of this invention. All such modifications and extensions are intended to be included within the true spirit and scope of the appended claims

What is claimed, is:

1. A method for setting messages on an electro-optic display for presentation, comprising:
   providing the electro-optic display, the electro-optic display comprising a single electro-optic layer comprising a material that irreversibly changes color, quality, or transparency from a first state to a permanent second state and a first electrode adjacent to and operably coupled to a first message surface of the electro-optic layer and second electrode adjacent to and operably coupled to an opposing second message surface, each message surface in a first state and can be independently activated to present a message;

applying at a first time a first signal across the electrodes to set a first message on the first message surface, the first message is set in a permanent second state that is irreversible to its first state; and the second state has a color, quality, or transparency different from the first state;

applying at a second time a second signal across the electrodes to set a second message on the second message surface, the second message is set in a permanent second state that is irreversible to its first state; and the second state has a color, quality, or transparency different from the first state; and wherein the second signal has a polarity different from the first signal.

2. The method of claim 1, wherein the second signal is applied at a lower voltage than the first signal or applied at a higher voltage than the first signal.

3. The method of claim 1, wherein the second signal is applied for a shorter duration than the first signal or applied for a longer duration than the first signal.

4. The method of claim 1, wherein the first or second signals are continuous, or the first or second signals are not continuous.

5. A method for setting messages on an electro-optic display for presentation, comprising:
providing the electro-optic display, the electro-optic display comprising a single electro-optic layer comprising a material that irreversibly changes color, quality, or transparency from a first state to a permanent second state and a first electrode adjacent to and operably coupled to a first message surface of the electro-optic layer and second electrode adjacent to and operably coupled to an opposing second message surface, each message surface in a first state and can be independently activated to present a message;

applying at a first time a first signal across the electrodes to set a first message on the first message surface;

applying at a second time a second signal across the electrodes that cooperates with the first signal to set the first message in a permanent second state that is irreversible to its first state; the second state having a color, quality, or transparency different from the first state;

applying at a third time a third signal across the electrodes to set a second message on the second message surface, the second message is set in a permanent second state that is irreversible to its first state; the second state having a color, quality, or transparency different from the first state; and wherein the second signal and the third signal have a different polarity from the first signal.

6. The method of claim 5, wherein the second signal is applied at a lower voltage than the first signal or at a higher voltage than the first signal.

7. The method of claim 5, wherein the second signal is of a shorter duration than the first signal or a longer duration of the first signal.

8. The method of claim 5, wherein the first or second signals are continuous, or the first or second signals are not continuous.

9. A method for setting messages on an electro-optic display for presentation, comprising:
providing the electro-optic display, the electro-optic display comprising a single electro-optic layer comprising a material that irreversibly changes color, quality, or transparency from a first state to a permanent second state and a first electrode adjacent to and operably coupled to a first message surface of the electro-optic layer and second electrode adjacent to and operably coupled to an opposing second message surface, each message surface in a first state and can be independently activated to present a message;

applying at a first time a first signal across the electrodes to set a first message on the first message surface;

applying at a second time a second signal across the electrodes that cooperates with the first signal to set the first message in a permanent second state that is irreversible to its first state; the second state having a color, quality, or transparency different from the first state;

applying at a third time a third signal across the electrodes to set a second message on the second message surface;

applying at a fourth time a fourth signal across the electrodes that cooperates with the third signal to set the second message in a permanent second state that is irreversible to its first state; the second state having a color, quality, or transparency different from the first state; the second message is set in a permanent second state that is irreversible to its first state; the second state having a color, quality, or transparency different from the first state; and wherein the second signal and the third signal have a different polarity from the first signal and the fourth signal.

10. The method of claim 9, wherein the second or fourth signals are of a lower voltage than the first or third signals or a higher voltage than the first or third signals.

11. The method of claim 9, wherein the second or fourth signals are of a shorter duration than the first or third signals or a longer duration of the first or third signals.

12. The method of claim 9, wherein the second or fourth signals are continuous, or the second or fourth signal are not continuous.

* * * * *